United States Patent [19]

Zeun et al.

[11] Patent Number: 5,536,726
[45] Date of Patent: Jul. 16, 1996

[54] MICROBICIDES

[75] Inventors: Ronald Zeun, Neuenburg; Gertrude Knauf-Beiter, Ehrenkirchen, both of Germany; Ruth B. Küng, Allschwil, Switzerland

[73] Assignee: Ciba-Geigy Corporation, Tarrytown, N.Y.

[21] Appl. No.: 417,172

[22] Filed: Apr. 5, 1995

Related U.S. Application Data

[62] Division of Ser. No. 266,063, Jun. 27, 1994, Pat. No. 5,430,035.

[30] Foreign Application Priority Data

Jun. 28, 1993 [CH] Switzerland ............... 1920/93
Jul. 16, 1993 [CH] Switzerland ............... 2154/93
Apr. 27, 1994 [CH] Switzerland ............... 1306/94

[51] Int. Cl.$^6$ .................. A01N 43/38; A01N 43/54
[52] U.S. Cl. .......................... 514/275; 514/421
[58] Field of Search .......................... 514/275, 421

[56] References Cited

U.S. PATENT DOCUMENTS

| | | | |
|---|---|---|---|
| 2,553,770 | 5/1951 | Kittleson | 167/33 |
| 4,229,465 | 10/1980 | Ohkuma et al. | 424/274 |
| 4,241,058 | 12/1980 | Pfiffner | 424/248.4 |
| 4,925,840 | 5/1990 | Nyfeler et al. | 514/228 |
| 4,931,560 | 6/1990 | Hubele | 544/315 |
| 5,112,849 | 5/1992 | Staub et al. | 514/427 |
| 5,166,395 | 11/1992 | Wollweber et al. | 558/401 |
| 5,330,984 | 7/1994 | Kurg et al. | 514/239.5 |
| 5,403,844 | 4/1995 | Mittermeir et al. | 525/330 |

FOREIGN PATENT DOCUMENTS

| | | |
|---|---|---|
| 2112287 | 7/1983 | United Kingdom. |
| 2267644 | 12/1993 | United Kingdom. |

OTHER PUBLICATIONS

Chemical Abstracts 96: 157395n (1982).

Primary Examiner—Allen J. Robinson
Attorney, Agent, or Firm—Edward McC. Roberts

[57] ABSTRACT

A plant-microbicidal composition having synergistic action, comprising at least two active ingredient components, wherein component I is a compound selected from the group IA) cis-4-[3-(4-tert-butylphenyl)-2-methylpropyl]-2,6-dimethylmorpholine (fenpropimorph"); and/or 1-[3-(4-tert-butylphenyl)-2-methylpropyl]-piperidine ("fenpropidin"), or one of the salts or metal complexes thereof;

IB) 4-(2,2-difluoro-1,3-benzodioxol-4-yl)-1H-pyrrole-3-carbonitrile ("fludioxonil");

IC) N-(trichloromethylthio)cyclohex-4-ene-1,2-dicarboximide("captan");

ID) a compound of formula ID

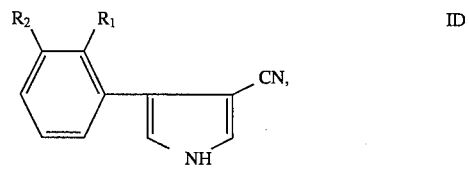

wherein $R_1$ is fluorine or chlorine and $R_2$ is chlorine or trifluoromethyl, and IE) N-(trichloromethylthio)phthalimide ("folpet");

and component II is the 2-anilinopyrimidine of formula II

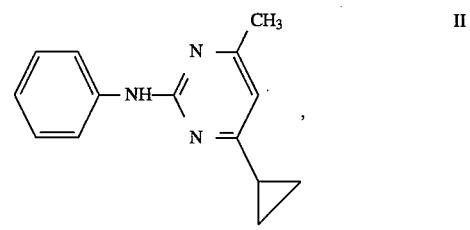

4-cyclopropyl-6-methyl-N-phenyl-2-pyrimidineamine, or one of the salts or metal complexes thereof.

8 Claims, No Drawings

MICROBICIDES

This application is a division of application Ser. No. 08/266,063, filed Jun. 27, 1994, now U.S. Pat. No. 5,430,035, issued Jul. 4 1995.

The present invention relates to novel microbicidal active-ingredient mixtures having synergistically enhanced action, comprising at least two active ingredient components, and to methods of using such mixtures in plant protection.

Component I is a compound selected from the group:

IA) cis-4-[3-(4-tert-butylphenyl)-2-methylpropyl]-2,6-dimethylmorpholine (fenpropimorph"); and/or 1-[3-(4-tert-butylphenyl)-2-methylpropyl]-piperidine ("fenpropidin"), or one of the salts or metal complexes thereof; (reference: DE 2 752 135);

IB ) 4-(2,2-difluoro-1,3-benzodioxol-4-yl)-1H-pyrrole-3-carbonitrile ("fludioxonil"; reference: EP-A-206 999);

IC) N-(trichloromethylthio)cyclohex-4-ene-1,2-dicarboximide ("captan"; reference: U.S. Pat. No. 2,553,770);

ID) compound of formula ID

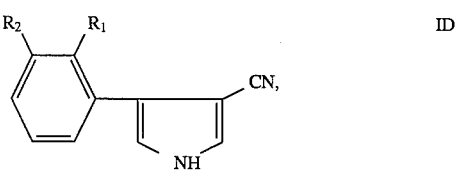

wherein $R_1$ is fluorine or chlorine and $R_2$ is chlorine or trifluoromethyl. (References: EP-A-236 272; DE 2 927 480); and IE) N-(trichloromethylthio)phthalimide ("folpet"; reference: U.S. Pat. No. 2,553,770).

Component II is the 2-anilinopyrimidine of formula

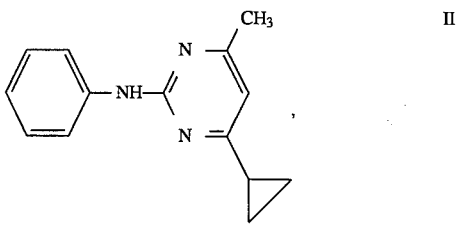

4-cyclopropyl-6-methyl-N-phenyl-2-pyrimidineamine, or one of the salts or metal complexes thereof (reference: EP-A-310 550).

Of the compounds of formula IA, preference is given to 1-[3-(4-tert-butylphenyl)- 2-methylpropyl]-piperidine ("fenpropidin").

Of the compounds of formula ID, preference is given to the compound wherein $R_1$ and $R_2$ are chlorine: 4-(2,3-dichlorophenyl)-1H-pyrrole-3-carbonitrile ("fenpiclonil").

Of the acids that can be used for the preparation of salts of formulae IA and II, the following may be mentioned:

hydrohalic acids, such as hydrofluoric acid, hydrochloric acid, hydrobromic acid or hydriodic acid; sulfuric acid, phosphoric acid, nitric acid; and organic acids, such as acetic acid, trifluoroacetic acid, trichloroacetic acid, propionic acid, glycolic acid, thiocyanic acid, lactic acid, succinic acid, citric acid, benzoic acid, cinnamic acid, oxalic acid, formic acid, benzenesulfonic acid, p-toluenesuffonic acid, methanesuffonic acid, salicylic acid, p-aminosalicylic acid, 2-phenoxybenzoic acid, 2-acetoxybenzoic acid and 1,2-naphthalene-disulfonic acid.

The term salts also includes metal complexes of basic components I and II. Those complexes may as desired involve only one component or the two components independently. It is also possible to produce metal complexes in which the two active ingredients I and II are linked together to form a mixed complex.

Metal complexes consist of the underlying organic molecule and an inorganic or organic metal salt, for example a halide, nitrate, sulfate, phosphate, acetate, trifluoroacetate, trichloroacetate, propionate, tartrate, sulfonate, salicylate, benzoate, etc., of an element of main group II, such as calcium and magnesium and of main groups III and IV, such as aluminium, tin or lead, and of subgroups I to VIII, such as chromium, manganese, iron, cobalt, nickel, copper, zinc, etc. Preference is given to the subgroup elements of the 4th period. The metals may have any of the different valencies in which they occur. The metal complexes can be mono- or poly-nuclear, i.e. they can contain one or more organic molecule components as ligands.

Further agrochemical active ingredients, such as insecticides, acaricides, nematicides, herbicides, growth regulators and fertilisers, but especially additional microbicides, may also be added to the active ingredient mixture according to the invention.

It has now been found, surprisingly, that the fungicidal action of mixtures of components I and II is not merely additive but is clearly synergistically enhanced.

The present invention therefore represents a very substantial enrichment of the art.

In addition, the present invention relates also to a method of controlling fungi which comprises treating a site infested by or threatened by infestation by fungi with, in any desired sequence or simultaneously, a) a compound of formula I or one of the salts thereof and b) the compound of formula II or one of the salts thereof, it being possible also for the salts to so selected that the two compounds are bonded to an acid radical or, in the case of a metal complex, to a central metal cation.

Advantageous mixing ratios of the two compounds are I:II= 1:20 to 10: 1, preferably I:II= 1:6 to 6:1.

Especially advantageous mixing ratios are

IA:II= 1:4 to 2:1
IB:II= 5:1 to 1:5
IC:II= 5:1 to 1:2
ID:II= 5:1 to 1:5
IE:II= 5:1 to 1:2.

The compound mixtures I+II according to the invention have very advantageous curative, preventive and systemic fungicidal properties for protecting plants. The compound mixtures of the invention can be used to inhibit or to destroy the microorganisms occurring on plants or on parts of plants (the fruit, blossom, leaves, stalks, tubers or roots) of different crops of useful plants, while at the same time parts of plants that grow later are also protected against such microorganisms. They can also be used as dressings in the treatment of plant propagation material, especially seed (fruit, tubers, grain) and plant cuttings (for example rice), to provide protection against fungal infections and against phytopathogenic fungi occurring in the soil. The compound mixtures according to the invention are distinguished by the fact that they are especially well tolerated by plants and are environmentally friendly.

The compound mixtures are effective against phytopathogenic fungi belonging to the following classes: Ascomycetes (e.g. Venturia, Podosphaera, Erysiphe, Monilinia, Uncinula); Basidiomycetes (e.g. the genera Hemileia, Rhizoctonia, Puccinia); Fungi impeffecti (e.g. Botrytis, Helminthosporium, Rhynchosporium, Fusarium, Septoria, Cercospora, Altemaria, Pyricularia and especially *Pseudocer-*

*cosporella herpotrichoides*); Oomyceten (z.B. Phytophthora, Pemospora, Bremia, Pythium, Plasmopara).

Target crops to be protected within the scope of the present invention comprise, for example, the following species of plants: cereals: (wheat, barley, rye, oats, rice, sorghum and related species); beets: (sugar beet and fodder beet); pomes, stone fruit and soft fruit: (apples, pears, plums, peaches, almonds, cherries, strawberries, raspberries and blackberries); leguminous plants: (beans, lentils, peas and soybeans); oil plants: (rape, mustard, poppy, olives, sunflowers, coconut, castor oil plants, cocoa beans and groundnuts); cucumber plants: (marrows, cucumber and melons); fibre plants: (cotton, flax, hemp and jute); citrus fruit: (oranges, lemons, grapefruit and mandarins); vegetables: (spinach, lettuce, asparagus, cabbages, carrots, onions, tomatoes, potatoes and paprika); lauraceae: (avocados, cinnamon and camphor); or plants such as maize, tobacco, nuts, coffee, sugar cane, tea, vines, hops, bananas and natural rubber plants, as well as ornamentals (flowers, shrubs, broad-leaved trees and evergreens, such as conifers). That list does not represent any limitation.

The compound mixtures according to the invention are especially advantageous for the following applications:

IA+II: in cereals, especially in wheat and barley;
IB+II: in vines and vegetables, and in the treatment of plant propagation material, such as seed, tubers and cuttings;
IC+II: in fruit and vegetables, especially apples and pears;
ID+II: in the treatment of plant propagation material, such as seed, tubers and cuttings;
IE+II: in vines and vegetables.

The mixtures of compounds of formulae I and II are generally used in the form of compositions. The compounds of formula I and the compound of formula II can be applied to the area or plant to be treated, either simultaneously or in succession on the same day, together with, where appropriate, further carriers, surfactants or other application-promoting adjuvants customarily employed in formulation technology.

Suitable carriers and adjuvants may be solid or liquid and are substances ordinarily employed in formulation technology, for example natural or regenerated mineral substances, solvents, dispersants, wetting agents, tackifiers, thickeners, binders or fertilisers.

A preferred method of applying a compound mixture comprising at least one of each of compounds I and II is application to the parts of the plants that are above the soil, especially to the leaves (foliar application). The frequency and rate of application depend on the biological and climatic living conditions of the pathogens. The compounds can, however, also penetrate the plants through the roots via the soil (systemic action) if the locus of the plant is impregnated with a liquid formulation, or if the compounds are introduced in solid form into the soil, e.g. in the form of granules (soil application). In order to treat the seed, the compounds of formulae I and II may also be applied to the seeds (coating) either by impregnating the tubers or grains in succession with liquid formulations each comprising one of the compounds or by coating them with an already combined wet or dry formulation. In addition, in special cases, other methods of application to plants are possible, e.g. treatment directed at the buds or the fruit.

The compounds of the combination are used in unmodified form or preferably together with the adjuvants conventionally employed in formulation technology, and are therefore formulated in known manner, e.g. into emulsifiable concentrates, coatable pastes, directly sprayable or dilutable solutions, dilute emulsions, wettable powders, soluble powders, dusts or granules, or by encapsulation in e.g. polymer substances. As with the nature of the compositions, the methods of application, such as spraying, atomising, dusting, scattering, coating or pouring, are chosen in accordance with the intended objectives and the prevailing circumstances. Advantageous rates of application of the active ingredient mixture are generally from 50 g to 2 kg a.i./ha, preferably from 100 g to 1000 g a.i./ha, especially from 400 g to 1000 g a.i./ha. In the case of the treatment of seed, the rates of application are from 0.5 g to 1000 g, preferably from 5 g to 100 g, a.i. per 100 kg of seed.

The formulations are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, such as xylene mixtures or substituted naphthalenes, phthalates, such as dibutyl or dioctyl phthalate, aliphatic hydrocarbons, such as cyclohexane, or paraffins, alcohols and glycols and their ethers and esters, such as ethanol, ethylene glycol, ethylene glycol monomethyl or monoethyl ether, ketones, such as cyclohexanone, strongly polar solvents, such as N-methyl-2-pyrrolidone, dimethyl sulfoxide or dimethylformamide, and vegetable oils or epoxidised vegetable oils, such as epoxidised coconut oil or soybean oil; and water.

The solid carriers used, e.g. for dusts and dispersible powders, are normally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are e.g. calcite or sand. In addition, a great number of pregranulated materials of inorganic or organic nature can be used, such as especially dolomite or pulverised plant residues.

Depending on the nature of the compounds of formulae I and II to be formulated, suitable surface-active compounds are non-ionic, cationic and/or anionic surfactants having good emulsifying, dispersing and wetting properties. The term "surfactants" will also be understood as comprising mixtures of surfactants.

The surfactants customarily used in formulation technology are found inter alia in the following publications:

"Mc Cutcheon's Detergents and Emulsifiers Annual" MC Publishing Corp., Glen Rock, N.J., 1988.

M. and J. Ash, "Encyclopedia of Surfactants", Vol. I—III, Chemical Publishing Co., New York, 1980–1981.

Especially advantageous application-promoting adjuvants are also natural or synthetic phospholipids from the series of cephalins and lecithins, such as phosphatidylethanolamine, phosphatidylserine, phosphatidylglycerol and lysolecithin.

The agrochemical compositions generally comprise 0.1 to 99%, preferably 0.1 to 95%, of compounds of formulae I and II, 99.9 to 1%, preferably 99.9 to 5%, of a solid or liquid adjuvant and 0 to 25%, preferably 0.1 to 25%, of a surfactant.

Whereas commercial products will preferably be formulated as concentrates, the end user will normally employ dilute formulations.

The present invention relates also to such (agro)chemical compositions.

The Examples that follow serve to illustrate the invention, "active ingredient" denoting a mixture of compound I and compound II in a specific mixing ratio.

| Formulation Examples |  |  |  |
|---|---|---|---|
| Wettable powders | a) | b) | c) |
| active ingredient [I:II = 1:3(a), 1:2(b), 1:1(c)] | 25% | 50% | 75% |
| sodium lignosulfonate | 5% | 5% | — |
| sodium laurylsulfate | 3% | — | 5% |
| sodium diisobutylnaphthalene-sulfonate | — | 6% | 10% |
| octylphenol polyethylene glycol ether (7–8 mol of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| Emulsifiable concentrate | |
|---|---|
| active ingredient (I:II = 1:6) | 10% |
| octylphenol polyethylene glycol ether (4–5 mol of ethylene oxide) | 3% |
| calcium dodecylbenzenesulfonate | 3% |
| castor oil polyglycol ether (35 mol of ethylene oxide) | 4% |
| cyclohexanone | 30% |
| xylene mixture | 50% |

Emulsions of any required concentration, which can be used in plant protection, can be obtained from this concentrate by dilution with water.

| Dusts | a) | b) | c) |
|---|---|---|---|
| active ingredient [I:II = 1:4 (a); 1:5 (b) and 1:1 (c)] | 5% | 6% | 4% |
| talcum | 95% | — | — |
| kaolin | — | 94% | — |
| mineral filler | — | — | 96% |

Ready-for-use dusts are obtained by mixing the active ingredient with the carrier and grinding the mixture in a suitable mill. Such powders can also be used for dry dressings for seed.

| Extruder granules | |
|---|---|
| active ingredient (I:II = 1:1.5) | 15% |
| sodium lignosulfonate | 2% |
| carboxymethylcellulose | 1% |
| kaolin | 82% |

The active ingredient is mixed and ground with the adjuvants, and the mixture is moistened with water. The mixture is extruded and then dried in a stream of air.

| Coated granules | |
|---|---|
| active ingredient (I:II = 3:5) | 8% |
| polyethylene glycol (mol. wt. 200) | 3% |
| kaolin | 89% |
| (mol. wt. = molecular weight) | |

The finely ground active ingredient is uniformly applied, in a mixer, to the kaolin moistened with polyethylene glycol. Non-dusty coated granules are obtained in this manner.

| Suspension concentrate | |
|---|---|
| active ingredient (I:II = 3:7) | 40% |
| propylene glycol | 10% |
| nonylphenol polyethylene glycol ether (15 mol of ethylene oxide) | 6% |
| sodium lignosulfonate | 10% |
| carboxymethylcellulose | 1% |
| silicone oil (in the form of a 75% aqueous emulsion) | 1% |
| water | 32% |

The finely ground active ingredient is intimately mixed with the adjuvants, giving a suspension concentrate from which suspensions of any desired concentration can be obtained by dilution with water. Such concentrations can be used to treat living plants and plant propagation material by spraying, pouring or immersion and to protect them against infestation by microorganisms.

Biological Examples

In the case of fungicities, a synergistic effect exists whenever the fungicidal action of the active ingredient combination is greater that the sum of the actions of the active ingredients applied individually.

The action E to be expected for a given active ingredient combination, e.g. of two fungicides, obeys the so-called COLBY formula and can be calculated as follows (COLBY, S. R. "Calculating synergistic and antagonistic responses of herbicide combination". Weeds, Vol. 15, pages 20–22; 1967):

ppm= milligram of active ingredient (=ai) per liter of spray mixture

X= % action by fungicide I using p ppm of active ingredient

Y= % action by fungicide II using q ppm of active ingredient and

E= the expected action of fungicities I+II using p+q ppm of active ingredient (additive action):

$$\text{according to Colby: } E = X + Y - \frac{X \cdot Y}{100}$$

If the action (O) actually observed is greater than the expected action (E), then the action of the combination is superadditive, i.e. there is a synergistic effect.

O/E= synergy factor (SF).

In the Examples that follow, the infestation of the untreated plants is said to be 100%, which corresponds to an action of 0%.

EXAMPLE 1

Action against *Botrytis cinerea* on Apples

Artificially damaged apples are treated by the dropwise application of a spray mixture (30 microliters of active ingredient or active ingredient combination) to the damaged area. The treated fruit are then inoculated with a spore suspension of the fungus and incubated for one week at high humidity at about 20° C. The fungicidal action of the test compound is calculated from the number and size of the damaged areas that have rotted. The following results are obtained:

TABLE 1

| | Compound IB: fludioxonil | | | | | |
|---|---|---|---|---|---|---|
| Test | mg ai per liter | | | % action found | calculated | SF |
| No. | ai IB | ai II | I:II | O | E | O/E |
| 0 | — | — | | 0 (control) | | |
| 1 | 0.2 | — | | 0 | | |
| 2 | 0.6 | — | | 20 | | |
| 3 | 2 | — | | 40 | | |
| 4 | 6 | — | | 90 | | |
| 5 | — | 0.2 | | 0 | | |
| 6 | — | 0.6 | | 0 | | |
| 7 | — | 2 | | 20 | | |
| 8 | — | 20 | | 95 | | |
| 9 | 0.6 | 2 | 1:3 | 40 | 36 | 1.1 |
| 10 | 0.6 | 0.2 | 3:1 | 40 | 20 | 2.0 |
| 11 | 2 | 0.2 | 10:1 | 98 | 40 | 2.4 |
| 12 | 2 | 0.6 | 3:1 | 98 | 40 | 2.4 |
| 13 | 2 | 2 | 1:1 | 95 | 52 | 1.8 |
| 14 | 6 | 0.2 | 30:1 | 100 | 90 | 1.1 |

EXAMPLE 2

Action against *Botrytis cinerea* on Vines 5-week-old vine seedlings are sprayed with a suspension prepared from a formulation of the test compound and infected after 2 days with a conidia suspension of *B. cinerea*. The seedlings are incubated for 4 days at 21° C. and 95–100% relative humidity in a greenhouse and the infestation is then assessed. The following results are obtained:

TABLE 2

| | Compound IB: fludioxonil | | | | | |
|---|---|---|---|---|---|---|
| Test | mg ai per liter | | | % action found | calculated | SF |
| No. | ai IB | ai II | I:II | O | E | O/E |
| 0 | — | — | | 0 (control) | | |
| 1 | 0.6 | — | | 0 | | |
| 2 | 2 | — | | 80 | | |
| 3 | 6 | — | | 90 | | |
| 4 | — | 0.2 | | 0 | | |
| 5 | — | 0.6 | | 0 | | |
| 6 | — | 2 | | 20 | | |
| 7 | — | 20 | | 90 | | |
| 8 | 2 | 0.6 | 3:1 | 90 | 80 | 1.12 |
| 9 | 0.6 | 0.2 | 3.1 | 20 | 0 | * |
| 10 | 2 | 0.2 | 10:1 | 98 | 80 | 1.22 |

*synergy factor SF cannot be calculated

EXAMPLE 3

Action against *Venturia inaequalis* on Apples

Apple cuttings with 10 to 20 cm long fresh shoots are sprayed to drip point with a spray mixture prepared from a formulation of the active ingredient or active ingredient combination. After 24 hours the treated plants are infected with a conidia suspension of the fungus. The treated plants are then incubated for 3 days at 90 to 100% relative humidity and 20° C. and then placed in a greenhouse for a further 10 days at 20 to 24° C. The infestation is assessed 14 days after infection. The following results are obtained:

TABLE 3a

| | Compound IB: fludioxonil | | | | | |
|---|---|---|---|---|---|---|
| Test | mg ai per liter | | | % action found | calculated | SF |
| No. | ai IB | ai II | I:II | O | E | O/E |
| 0 | — | — | | 0 (control) | | |
| 1 | 2 | — | | 40 | | |
| 2 | — | 2 | | 20 | | |
| 3 | 2 | 2 | 1:1 | 73 | 52 | 1.4 |

TABLE 3b

| | Compound IC: captan | | | | | |
|---|---|---|---|---|---|---|
| Test | mg ai per liter | | | % action found | calculated | SF |
| No. | ai IC | ai II | I:II | O | E | O/E |
| 0 | — | — | | 0 (control) | | |
| 1 | 10 | — | | 0 | | |
| 2 | 25 | — | | 0 | | |
| 3 | 50 | — | | 42 | | |
| 4 | 100 | — | | 60 | | |
| 5 | 150 | — | | 91 | | |
| 6 | 250 | — | | 94 | | |
| 7 | — | 1 | | 11 | | |
| 8 | — | 5 | | 16 | | |
| 9 | — | 10 | | 74 | | |
| 10 | — | 25 | | 94 | | |
| 11 | — | 50 | | 98 | | |
| 12 | 10 | 1 | 10:1 | 49 | 11 | 4.5 |
| 13 | 10 | 5 | 2:1 | 56 | 16 | 3.5 |
| 14 | 50 | 5 | 10:1 | 75 | 51 | 1.5 |

EXAMPLE 4

Action against *Puccinia recondita* on Wheat 10-day-old wheat plants are sprayed to drip point with a spray mixture prepared from a formulation of the active ingredient or active ingredient combination. After 24 hours the treated plants are infected with a conidia suspension of the fungus. The treated plants are then incubated for 2 days at 90–100% relative humidity and at 20° C. 2 weeks after infection the fungal infestation is assessed. The following results are obtained:

TABLE 4

| | Compound IA: fenpropidin | | | | | |
|---|---|---|---|---|---|---|
| Test | mg ai per liter | | | % action found | calculated | SF |
| No. | ai IA | ai II | I:II | O | E | O/E |
| 0 | — | — | | 0 (control) | | |
| 1 | 125 | — | | 5 | | |
| 2 | 250 | — | | 73 | | |
| 3 | — | 250 | | 5 | | |
| 4 | — | 500 | | 10 | | |
| 5 | — | 1000 | | 46 | | |
| 6 | 125 | 250 | 1:2 | 19 | 10 | 1.9 |
| 7 | 125 | 500 | 1:4 | 53 | 15 | 3.5 |
| 8 | 125 | 1000 | 1:8 | 70 | 49 | 1.4 |

EXAMPLE 5

Action against *Erysiphe graminis* on Barley 7-day-old barley plants are sprayed to drip point with a spray mixture prepared from a formulation of the active ingredient or active ingredient combination. After 1 day the plants are inoculated with a conidia suspension of *Erysiphe graminis* and incubated in a greenhouse at 21° C. and 50–80% humidity. After one week the fungal infestation is assessed. The following results are obtained:

TABLE 5

Compound IA: fenpropidin

| Test No. | mg ai per liter | | | % action found | calculated | SF |
|---|---|---|---|---|---|---|
| | ai IA | ai II | I:II | O | E | O/E |
| 0 | — | — | | 0 (control) | | |
| 1 | 2 | — | | 0 | | |
| 2 | 10 | — | | 49 | | |
| 3 | 20 | — | | 76 | | |
| 4 | 100 | — | | 99 | | |
| 5 | 200 | — | | 100 | | |
| 6 | — | 20 | | 0 | | |
| 7 | — | 100 | | 7 | | |
| 8 | — | 200 | | 34 | | |
| 9 | — | 400 | | 59 | | |
| 10 | 2 | 20 | 1:10 | 55 | 0 | * |
| 11 | 10 | 100 | 1:10 | 73 | 52 | 1.4 |
| 12 | 20 | 100 | 1:5 | 94 | 78 | 1.2 |

*synergy factor SF cannot be calculated

EXAMPLE 6

Action against *Pyrenophora teres* on Barley 6-day-old barley plants are sprayed to drip point with a spray mixture prepared from a formulation of the active ingredient or active ingredient combination. After 2 days the plants are inoculated with a spore suspension of *Pyrenophora teres* and incubated in a greenhouse at 21° C. and 90–100% humidity. After one week the fungal infestation is assessed. The following results are obtained:

TABLE 6

Compound IB: fludioxonil

| Test No. | mg ai per liter | | | % action found | calculated | SF |
|---|---|---|---|---|---|---|
| | ai IB | ai II | I:II | O | E | O/E |
| 0 | — | — | | 0(control) | | |
| 1 | 0.6 | — | | 0 | | |
| 2 | 2 | — | | 75 | | |
| 3 | 6 | — | | 80 | | |
| 4 | — | 0.6 | | 0 | | |
| 5 | — | 2 | | 20 | | |
| 6 | — | 20 | | 85 | | |
| 7 | 0.6 | 0.6 | 1:1 | 40 | 0 | * |
| 8 | 0.6 | 2 | 1:3 | 40 | 20 | 2 |
| 9 | 6 | 0.2 | 30:1 | 95 | 80 | 1.2 |

*synergy factor SF cannot be calculated

What is claimed is:

1. A plant-microbicidal composition comprising synergistic fungicidally effective amounts of two active ingredient components, wherein component I is N-(trichloromethylthio)cyclohex-4-ene-1,2-dicarboximide ("captan") and component II is the anilinopyrimidine of formula II

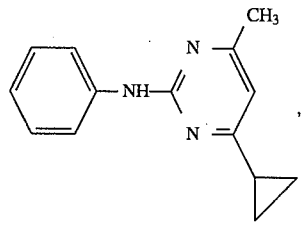

4-cyclopropyl-6-methyl-N-phenyl-2-pyrimidineamine, or a salt or metal complex thereof together with an inert carrier, wherein the weight ratio of the active ingredients I and II is in the range of 2:1 to 10:1.

2. A method of controlling and preventing the occurrence of fungi on plants, which comprises treating with synergistic fungicidally effective amounts of component I and component II according to claim 1, in any desired order or simultaneously, a site infested by or threatened with infestation by fungi.

3. A method according to claim 2 wherein plant propagation material is treated.

4. A method according to claim 3 wherein seed is treated.

5. A plant-microbicidal composition comprising synergistic fungicidally effective amounts of two active ingredient components, wherein component I is N-(trichloromethylthio)cyclohex-4-ene-1,2-dicarboximide ("captan") and component II is the anilinopyrimidine of formula II

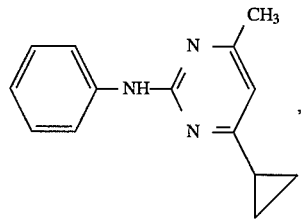

4-cyclopropyl-6-methyl-N-phenyl-2-pyrimidineamine, or a salt or metal complex thereof together with an inert carrier, wherein the weight ratio of the active ingredients I and II is in the range of 1:6 to 6:1.

6. A method of controlling and preventing the occurrence of fungi on plants, which comprises treating with synergistic fungicidally effective amounts of component I and component II according to claim 5, in any desired order or simultaneously, a site infested by or threatened with infestation by fungi.

7. A method according to claim 6 wherein plant propagation material is treated.

8. A method according to claim 7 wherein seed is treated.

* * * * *